United States Patent
Arditi et al.

(10) Patent No.: US 7,959,918 B2
(45) Date of Patent: Jun. 14, 2011

(54) METHODS FOR TREATING VASCULAR DISEASE

(75) Inventors: Moshe Arditi, Encino, CA (US); Tripathi Rajavashisth, El Camino Village, CA (US); Prediman K. Shah, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 413 days.

(21) Appl. No.: 11/569,241

(22) PCT Filed: May 25, 2005

(86) PCT No.: PCT/US2005/018604
§ 371 (c)(1),
(2), (4) Date: Jul. 25, 2008

(87) PCT Pub. No.: WO2005/117975
PCT Pub. Date: Dec. 15, 2005

(65) Prior Publication Data
US 2008/0286285 A1    Nov. 20, 2008

Related U.S. Application Data

(60) Provisional application No. 60/575,665, filed on May 28, 2004.

(51) Int. Cl.
*A61K 39/395* (2006.01)
*C07K 16/28* (2006.01)
*C07C 57/00* (2006.01)

(52) U.S. Cl. .................. 424/144.1; 530/388.22; 562/496

(58) Field of Classification Search .......................... None
See application file for complete search history.

(56) References Cited

U.S. PATENT DOCUMENTS

| | | | |
|---|---|---|---|
| 6,323,334 B1 * | 11/2001 | Kingsbury et al. | 536/23.5 |
| 7,312,320 B2 | 12/2007 | Elson | |
| 2003/0077279 A1 * | 4/2003 | Arditi et al. | 424/144.1 |
| 2003/0148986 A1 * | 8/2003 | Arditi et al. | 514/44 |
| 2003/0232352 A1 | 12/2003 | Schwartz et al. | |

FOREIGN PATENT DOCUMENTS

| WO | 03/050137 A2 | 6/2003 |
|---|---|---|
| WO | 2004/031225 A1 | 4/2004 |
| WO | 2004/093778 A2 | 11/2004 |

OTHER PUBLICATIONS

Bjorbacka H., et al. Reduced atherosclerosis in MyD88-null mice links elevated serum cholesterol levels to activation of innate immunity signaling pathways. Nature Medicine, 2004, vol. 10, No. 4, p. 416-421.*
Bartfai T., et al. A low molecular weight mimic of the Toll/IL-1 receptor/resistance domain inhibits IL-1 receptor-mediated responses. Proc. Natl. Acad. Sci. USA, 2003, vol. 100, No. 13, p. 7971-7976.*
Burns K., et al. MyD88, an adapter protein involved in interleukin-1 signaling. J. Biol. Chem. 1998, vol. 273, No. 20, p. 12203-12209.*
Pasterkamp, et al. "Role of Toll-like receptor 4 in the initiation and progression of atherosclerotic disease", European Journal of Clinal Investigation (2004) 34, 328-334.*
Fort M.M, et al. "A synthetic TLR4 antagonist has anti-inflammatory effects in two murine models of inflammatory bowel disease", J. Immumnolgy, 2005, vol. 174, p. 6416-6423.*
Van Tassell B.W., et al. "Pharmacological inhibition of myeloid differentiation factor 88 (MyD88) prevents left ventricular dilation and hypertrophy after experimental acute myocardial infarction in the mouse", J. Cardiovascular Pharmacology, 2010, vol. 55, p. 385-390.*
Gupta B, et al. "Intracellular delivery of large molecules and small particles by cell-penetrating proteins and peptides", Advanced Drug Delivery Reviews, 2005, vol. 57, p. 637-651.*
Fitzgerald K.A., et al. "Mal (MyD88-adapter-like) is required for Toll-like receptor-4 signal transduction", Nature, 2001, vol. 413, p. 78-83.*
Ronni T, et al. "Common interaction surfaces of the toll-like receptor 4 cytoplasmic domain stimulate multiple nuclear targets", Molecular and Cellular Biology, 2003, vol. 23, p. 2543-2555.*
Burns, K. et al., MyD88, an Adapter Protein Involved in Interleukin-1 Signaling, Journal of Biological Chemistry, May 15, 1998, 273:20, pp. 12203-12209.
Ulevitch, R.J. et al., Therapeutics Targeting the Innate Immune System, Immunology, Jul. 1, 2004, 4:7, pp. 512-520.
Zuan-Amorim, C. et al., Toll-Like Receptors as Potential Therapeutic Targets for Multiple Diseases, Nature Reviews/Drug Discovery, Oct. 2002, pp. 797-807.
International Search Report and Written Opinion, PCT/US09/50317; Dec. 10, 2009.
Kim, et al. "Crystal structure of the TLR4-MD-2 complex with bound endotoxin antagonist eritoran," Cell, vol. 130, Sep. 7, 2007; 906-907.
Ohta, et al. "Identification of a novel isoform of MD-2 that downregulates lipopolysaccharide signaling," Biochemical and Biophysical Research Communications, vol. 323 (2004); 1103-1108.
Shimazu, et al. "MD-2, a molecule that confers lipopolysaccharide responsiveness on toll-like receptor 4," Journal of Experimental Medicine, vol. 189, No. 11, Jun. 7, 1999; 1777-1782.

* cited by examiner

*Primary Examiner* — Robert Landsman
*Assistant Examiner* — Bruce D Hissong
(74) *Attorney, Agent, or Firm* — Seth D. Levy; Davis Wright Tremaine LLP (57) ABSTRACT

Compositions and methods included herein describe the treatment of atherosclerosis and other vascular diseases such as thrombosis, restenosis after angioplasty and/or stenting, and vein-graft disease after bypass surgery, by inhibition of the expression or biologic activity of the toll-like receptor 4 (TLR4) and/or myeloid differentiation factor 88 (MyD88). TLR4 cell signal transduction is at least partially responsible for the manifestation, continuation, and/or worsening of atherosclerosis and other forms of vascular disease. The present invention provides several means with which to inhibit this signal transduction pathway by affecting the biological activity of the TLR4 receptor and/or MyD88.

13 Claims, 5 Drawing Sheets

Apoe-/-
MyD88+/+

Fig. 2C

Apoe-/-
MyD88+/-

Fig. 2D

Apoe-/-
MyD88-/-

METHODS FOR TREATING VASCULAR DISEASE

This application is the National Phase of International Application PCT/US05/18604, filed May 25, 2005, which designated the U.S. and that International Application was published under PCT Article 21(2) in English. This application also includes a claim of priority under 35 U.S.C. §119(e) to U.S. provisional patent application No. 60/575,665, filed May 28, 2004.

GOVERNMENT RIGHTS

The invention described herein arose in the course of or under Grant Nos. HL-51087, Al-50699, and 1R01HL066436-01 between the National Institutes of Health and Dr. Moshe Arditi, Division of Pediatric Infectious Diseases at Cedars-Sinai Medical Center.

FIELD OF THE INVENTION

The present invention relates generally to signal transduction pathways. More particularly, the invention relates to antagonists of toll-like receptor 4 (TLR4) and myeloid differentiation factor 88 (MyD88) function.

BACKGROUND OF THE INVENTION

Heart disease remains the leading cause of death worldwide, accounting for nearly 30% of the annual total (i.e., approximately 15 million people). Heart and vascular disease debilitate many more individuals every year. For many, atherosclerotic disease is a life-long process; it may possess an initial stage in childhood, without clinical manifestation until middle age or later. Its development has been repeatedly linked to unhealthy lifestyles (e.g., tobacco use, unbalanced diet, and physical inactivity). Much progress has been made in the detection and treatment of various forms of heart and vascular disease, but preventative measures and assorted treatment regimens are usually incapable of halting or curing the underlying disease condition.

Atherosclerosis is now recognized to be a chronic inflammatory disease characterized by subendothelial accumulation of atherogenic lipoproteins, extracellular matrix, neovessels, calcium, and inflammatory cells. Activation of inflammatory genes in the vessel wall with subsequent adhesion, chemoattraction, subendothelial migration, retention, and activation of inflammatory and immune cells such as monocytes and T cells are believed to play a critical role in the initiation, progression, and destabilization of atherosclerosis (Ross, R. (1999) *N. Engl. J. Med.* 340, 115-126; Glass, C. K. & Witztum, J. L. (2001) *Cell* 104, 503-516; Shah, P. K. (2003) *J. Am. Coll. Cardiol.* 41, 15S-22S; Libby, P. (2002) *Nature* 420, 868-874; Hansson, G. K., et al. (2002) *Circ. Res.* 91, 281-291; Binder, C. J., et al. (2002) *Nat. Med.* 8, 1218-1226). Increasing interest has focused on the potential role of infectious agents and components of the innate immune system as contributors to atherosclerosis (Kol, A. & Libby, P. (1998) *Trends Cardiovasc. Med.* 8, 191-199), but clinical trials investigating treatment of cardiovascular diseases with antibiotics have produced conflicting results (Sander, D., et al., (2004) *Circulation* 109, 1010-1015; Zahn, R., et al. (2003) *Circulation* 107, 1253-1259; Sander, D., et al. (2002) *Circulation* 106, 2428-2433), perhaps because of inadequate power to detect differences or other shortcomings (Grayston, J. T. (2003) *Circulation* 107, 1228-1230).

Notwithstanding clinical disappointments, experimental evidence has accumulated that suggests that with enhanced understanding, treatment of cardiovascular disease with antibiotics and/or immunization may one day become feasible (Fredrikson, G. N., et al. (2003) *Arterioscler. Thromb. Vasc. Biol.* 23, 879-884; Binder, C. J., et al. (2003) *Nat. Med.* 9, 736-743; Hansson, G. K. (2002) *Circulation* 106, 1599-1601). In particular, intriguing data from animal studies suggest the potential importance of toll-like receptors (TLRs) and other key components of the innate immune system in atherosclerosis-based pathologies (Michelsen, K. S. et al. (2004) *J. Immunol.* 173, 5901-5907; de Kleijn, D. & Pasterkamp, G. (2003) *Cardiovasc. Res.* 60, 58-67). TLRs are a family of receptors that activate proinflammatory signaling pathways in response to microbial pathogens or pathogen-associated molecular patterns. Ligand binding to TLRs results in the recruitment of the adaptor molecule myeloid differentiation factor 88 (MyD88) to the toll/IL-1 receptor domain of the receptor. Intracellular propagation of the signal leads to activation of the transcription factor NF-κB, thereby influencing inflammatory responses (Zhang, G. & Ghosh, S. (2001) *J. Clin. Invest.* 107, 13-19). Furthermore, studies have shown that TLRs that signal through MyD88 are essential in proinflammatory cytokine responses to many microbial pathogens. Del Rio, L. et al. (2004) *J Immunol.* 172, 6954-60. MyD88 is an adapter protein necessary for the biochemical signaling attributed to a variety of cell receptors, including, by way of example, TLRs such as TLR4, as well as interleukin-1 (IL-1) and interleukin-18 (IL-18).

Studies have shown that human and murine lipid-rich atherosclerotic plaques express TLR4, and that TLR4 expression in macrophages is up-regulated by oxidized but not native low-density lipoprotein (LDL) (Xu, X. H., et al., (2001) *Circulation* 104, 3103-3108; Edfeldt, K., et al. (2002) *Circulation* 105, 1158-1161). In vitro studies have demonstrated that minimally modified LDL (MM-LDL), a proinflammatory and proatherogenic lipoprotein, is recognized by TLR4 and the coreceptor CD14 on macrophages, and binding of this lipoprotein leads to actin polymerization and spreading of macrophages (Miller, Y. I., et al. (2003) *J. Biol. Chem.* 278, 1561-1568). In human endothelial cells (ECs), the recognition of MM-LDL by TLR4 results in the secretion of IL-8, a chemokine important in monocyte transmigration and retention in the vessel wall (Walton, K. A., et al. (2003) *J. Biol. Chem.* 278, 29661-29666). However, this effect of MM-LDL was CD14-independent. Patients expressing a polymorphism in the TLR4 gene manifest lipopolysaccharide (LPS) hyporesponsiveness, are protected from carotid artery atherosclerosis and acute coronary events (Arbour, N. C., et al., (2000) *Nat. Genet.* 25, 187-191; Kiechl, S., et al. (2002) *N. Engl. J. Med.* 347, 185-192; Kiechl, S., et al., (2003) *Ann. Med.* 35, 164-171; Ameziane, N., et al. (2003) *Arterioscler. Thromb. Vasc. Biol.* 23, 61-64), and derive greater benefit from risk reduction with statins (Boekholdt, S. M., et al. (2003) *Circulation* 107, 2416-2421). Collectively, these findings suggest that TLR signaling may play a role in the development of atherosclerotic plaques.

Conventional treatments for vascular disease have substantial drawbacks; many are only partially effective, and few provide a true cure for associated conditions. There remains a clear need in the art for a method of preventing, treating, and curing vascular disease, including atherosclerosis.

The disclosures of all documents referred to throughout this application are incorporated herein by reference.

The foregoing examples of the related art and limitations related therewith are intended to be illustrative and not exclusive. Other limitations of the related art will become apparent to those of skill in the art upon a reading of the specification and a study of the drawings.

SUMMARY OF THE INVENTION

The following embodiments and aspects thereof are described and illustrated in conjunction with compositions and methods which are meant to be exemplary and illustrative, not limiting in scope. In various embodiments, one or more of the above-described problems have been reduced or eliminated, while other embodiments are directed to other improvements.

Toll-like receptor 4 (TLR4) and myeloid differentiation factor 88 (MyD88) are known to be involved in the signal transduction pathways for various disease conditions including, for example, atherosclerosis. In various embodiments, compositions and methods for inhibiting the function of TLR4 and MyD88 signal transduction pathways by administering TLR4 and/or MyD88 inhibitors are disclosed.

An embodiment by way of non-limiting example includes methods for inhibiting the biological activity of toll-like receptor 4 ("TLR4") and/or myeloid differentiation factor 88 ("MyD88"), as, for example, by inhibiting its expression or signaling. It is further an embodiment by way of non-limiting example to provide methods of treating those diseases in which inhibiting TLR4 and/or MyD88 would have a beneficial effect. Such diseases include, for example, vascular disease such as atherosclerosis and thrombosis, restenosis after angioplasty and/or stenting, and vein-graft disease after bypass surgery.

Another embodiment by way of non-limiting example includes a method to inhibit the MyD88 cell-signaling pathway using various peptide mimetics. This method involves the introduction of small peptides (i.e., peptides of approximately 10-20 amino acids) that bind to TLR4 receptors, thereby preventing TLR4 receptors from binding to or otherwise triggering MyD88 signaling cascades. In this manner, MyD88 signaling may be blocked, because the TLR4 receptors are unable to properly bind to MyD88.

Similarly, another embodiment by way of non-limiting example includes a method to inhibit the TLR4 cell-signaling pathway using various peptide mimetics. This method involves the introduction of small peptides (i.e., peptides of approximately 10-20 amino acids) that bind to endogenous MyD88, thereby preventing endogenous MyD88 from binding to or otherwise triggering TLR4 signaling cascades. In this manner, TLR4 signaling may be blocked, because the available TLR4 mimetics compete for available endogenous MyD88.

Another embodiment by way of non-limiting example includes a method to inhibit the expression of TLR4 and/or MyD88 through the introduction of an anti-TLR4 and/or an anti-MyD88 antibody. Such an antibody may be delivered to a mammal through any conventional mechanism in an amount effective to inhibit TLR4 and/or MyD88 signaling in a mammal.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 1 shows that MyD88 and TLR4 deficiency reduces the extent of aortic atherosclerosis in accordance with an embodiment of the invention.

FIG. 2 shows that Lipid content, macrophage infiltration, and COX-2 expression in aortic sinus plaques is reduced in ApoE−/−/MyD88−/− mice in accordance with an embodiment of the invention.

FIG. 3 shows that the serum concentration of IL-12p40 and monocyte chemoattractant protein 1 (MCP-1) are reduced in ApoE−/−/MyD88−/− mice in accordance with an embodiment of the invention.

FIG. 5 shows that TLR4 deficiency reduces the extent of macrophage infiltration and MCP-1 secretion in accordance with an embodiment of the invention.

DETAILED DESCRIPTION

The embodiments discussed herein are based on compositions and methods for inhibiting toll-like receptor-4 (TLR4) and myeloid differentiation factor 88 (MyD88) activity and expression. In various embodiments, these methods can be used to treat any disease in which inhibiting TLR4 and/or MyD88 activity has a beneficial effect on a patient (e.g., ameliorating a disease, lessening the severity of its complications, preventing it from manifesting, preventing it from recurring, merely preventing it from worsening, or a therapeutic effort to affect any of the aforementioned, even if such therapeutic effort is ultimately unsuccessful). Diseases are known in the art in which TLR4 and/or MyD88 activity is known or suspected to play a role in initiating, aggravating, or maintaining the pathological state that comprises the disease. Atherosclerosis, restenosis, inflammation and other vascular diseases are examples. Methods of the present invention may be used to treat any of these diseases.

Accumulating evidence implicates a fundamental link between the immune system and atherosclerosis, but thus far this evidence has been mostly indirect. As demonstrated herein, genetic deficiency of either MyD88 or TLR4 reduced aortic atherosclerosis in ApoE-deficient mice. Furthermore, MyD88 or TLR4 deficiency was associated with alterations in plaque composition that suggest greater structural stability. This is evidenced by a reduction in lipid and macrophage content, and markedly decreased expression of the proinflammatory enzyme, COX-2. Cell culture studies with endothelial cells (ECs) derived from mice with or without genetic MyD88 deficiency showed that leukocyte-EC adhesion was markedly hindered by genetic deficiency of MyD88. Finally, it was shown that the atheroprotective effect of MyD88 or TLR4 deficiency is not secondary due to altered serum cholesterol or lipoproteins. Still further, the findings of reduced circulating proinflammatory cytokine IL-12 and monocyte chemoattractant protein 1 (MCP-1) suggest that the atheroprotective effects of MyD88 and TLR4 deficiency may result in part from reduced systemic inflammation. Collectively, these results directly indicate that innate immune signaling has both systemic and local effects that together markedly inhibit development of atherosclerosis and promote a more stable plaque phenotype.

MyD88 is thought to transduce signals of all of the TLRs (except for TLR3), as well as the IL-1 and IL-18 receptors. Previous studies (Kirii, H., et al. (2003) *Arterioscler. Thromb. Vasc. Biol.* 23, 656-660) using IL-1β-deficient mice on an ApoE−/− background found a modest 30% decrease in the extent of atherosclerosis, which is considerably less than the nearly 60% reduction observed in the results discussed herein with mice deficient in both MyD88 and ApoE (FIG. 1). This finding suggests that MyD88 signaling mediates downstream proatherogenic effects in addition to those depending on intact IL-1β signaling. The results with ApoE−/−/TLR4−/− mice, which have intact IL-1β signaling, are consistent with this interpretation. In comparison with ApoE−/−/MyD88−/− mice, ApoE−/−/TLR4−/− mice display a more moderate but significant reduction in atherosclerotic lesions (57% vs. 24%, respectively) and a sustained reduction in macrophage infiltration and MCP-1 serum concentration. However, this moderate reduction was not unexpected. Atherosclerosis is multifactorial, dynamic, and highly variable temporally and spatially within the vasculature. Whereas there are many important contributors, there is no single culprit cause that accounts for the overwhelming variance in either the prevalence or extent of the disease. The results discussed herein are consistent with these notions, and demonstrate that TLR4 and MyD88 signaling is one contributor, but also directly shows that innate immune mechanisms are important contributors to the pathobiology of the disease rather than being secondarily associated with it. In addition, other TLRs using MyD88 may also be involved in atherogenesis. Recently, several bacterial or viral microorganisms have been postulated to be involved in atherogenesis, which contain ligands for TLR2, for instance (Binder, C. J., et al. (2002) *Nat. Med.* 8, 1218-1226; Libby, P., Ridker, P. M. & Maseri, A. (2002) *Circulation* 105, 1135-1143; Muhlestein, J. B. & Anderson, J. L. (2003) *Cardiol. Clin.* 21, 333-362).

MyD88 deficiency has been associated with a shift toward a T helper type 2 response (Schnare, M., et al. (2001) *Nat. Immunol.* 2, 947-950; Muraille, E., et al. (2003) *J. Immunol.* 170, 4237-4241; Kaisho, T., et al. (2002) *Int. Immunol.* 14, 695-700). In accord with this concept, observations were made that MyD88 deficiency was associated with reduced serum concentrations of IL-12p40. COX-2, IL-12, and MCP-1 were also examined because all are implicated in atherogenesis and are downstream targets of TLR4 and MyD88 signaling (Alexopoulou, L., et al. (2001) *Nature* 413, 732-738; Rhee, S. H. & Hwang, D. (2000) *J. Biol. Chem.* 275, 34035-34040; Kawai, T., et al. (2001) *J. Immunol.* 167, 5887-5894). Because IL-12 is directly linked to progression of atherosclerosis in mice, reduced IL-12p40 levels observed in MyD88-deficient, but not in TLR4-deficient mice could, in part, account for the further reduction of atherosclerosis observed in ApoE−/−/MyD88−/− mice (Lee, T. S., et al. (1999) *Arterioscler. Thromb. Vasc. Biol.* 19, 734-742; Davenport, P. & Tipping, P. G. (2003) *Am. J. Pathol.* 163, 1117-1125). TLR4 or MyD88 deficiency was also associated with a marked reduction in circulating levels of MCP-1, a key proatherogenic chemokine (Boring, L., et al. (1998) *Nature* 394, 894-897; Gu, L., et al. (1998) *Mol. Cell* 2, 275-281). MCP-1 deficiency may also have contributed to reduced atherosclerosis in ApoE−/−/MyD88−/− and ApoE−/−/TLR4−/− mice, because recent work has shown that genetic deficiency of MCP-1 (or its receptor CCR2) is associated with reduced macrophage infiltration and atherosclerosis in ApoE or LDL receptor-deficient mice (Boring, L., et al. (1998) *Nature* 394, 894-897; Gu, L., et al. (1998) *Mol. Cell* 2, 275-281). Furthermore, a recent study showed that unstable angina and acute myocardial infarction are associated with enhanced expression and signaling events downstream of hTLR4 in circulating monocytes suggesting that hTLR4 activation is a signaling mechanism in immune-mediated progression of atherosclerosis (Methe, H. et al., (2005) *Circulation*).

Increased expression of COX-2 in atherosclerotic lesions together with pharmacologic and direct genetic evidence suggest that COX-2 promotes atherosclerotic lesion formation (Schonbeck, U., et al., (1999) *Am. J. Pathol.* 155, 1281-1291; Burleigh, M. E., et al. (2002) *Circulation* 105, 1816-1823; Rott, D., et al. (2003) *J. Am. Coll. Cardiol.* 41, 1812-1819; Belton, O. A., et al. (2003) *Circulation* 108, 3017-3023; Olesen, M., et al. (2002) *Scand. Cardiovasc. J.* 36, 362-367; Verma, S., et al. (2001) *Circulation* 104, 2879-2882). Consistent with these data, it was found that MyD88 deficiency resulted in a marked reduction in COX-2 immunoreactivity in atherosclerotic plaques. This result might at least partially account for the inhibition of atherosclerosis observed in the ApoE–/–/MyD88–/– mice.

One of the key early events in the process of atherogenesis is enhanced leukocyte-EC adhesion. It was found that MyD88-deficient ECs demonstrated an impaired ability to support leukocyte adhesion in response to MM-LDL stimulation but not to TNF-α stimulation. Previous data (Shi, W., et al. (2000) Circ. Res. 86, 1078-1084) suggested that ECs from C57BL/6J mice exhibited substantial induction of proinflammatory molecules in response to MM-LDL, whereas ECs from C3H/HeJ mice did not. Together, these data suggest that MyD88 might regulate expression and/or function of cellular adhesion molecules on ECs, mononuclear phagocytes, or both. However, the possibility that MyD88 and/or TLR4 might also affect processes such as monocyte to macrophage conversion, or survival or retention of mononuclear phagocytes within the arterial wall cannot be excluded.

The evidence for involvement of NF-κB in the development of atherosclerosis is substantial (Collins, T. & Cybulsky, M. I. (2001) J. Clin. Invest. 107, 255-264). A recent study reported that macrophage-specific inhibition of the NF-κB pathway leads to more severe atherosclerosis in mice, perhaps due to a reduction in IL-10 production by macrophages (Kanters, E., et al. (2003) J. Clin. Invest. 112, 1176-1185). However, as discussed herein, there were no differences in IL-10 expression in ApoE–/–/MyD88–/– mice compared with littermate controls. More recently, it was reported that bone marrow transplants of p50-deficient donor mice into proatherogenic LDL receptor-null recipient mice leads to a decrease of atherosclerosis (Kanters, E., et al. (2004) Blood 103, 934-940). As evidenced, the involvement of NF-κB in atherosclerosis is not fully elucidated.

The results discussed herein contrast with previous reports (Wright, S. D., et al. (2000) J. Exp. Med. 191, 1437-1442), which suggested there was no difference in the extent of atherosclerosis between ApoE–/– and ApoE–/–/lps$^d$ mice—a strain generated by backcrossing ApoE–/– and the LPS-hyporesponsive strain C57BL/10ScN. However, the results discussed herein directly measured atherosclerosis, whereas the noted study (Wright, S. D., et al. (2000) J. Exp. Med. 191, 1437-1442) estimated atherosclerotic burden from cholesteryl ester content in whole aortas. Additionally, ApoE–/–/lps$^d$ mice only partially reflect a TLR4–/– genotype because they also lack two additional genes with unknown function (Qureshi, S. T., et al. (1999) J. Exp. Med. 189, 615-625). Furthermore, a different LPS-hyporesponsive strain C3H/HeJ that has nonfunctional TLR4 because of a spontaneous mutation (Poltorak, A., et al. (1998) Science 282, 2085-2088), is resistant to development of atherosclerosis (Shi, W., et al. (2000) Circ. Res. 86, 1078-1084), a finding that is consistent with the results discussed herein.

In sum, the various embodiments discussed herein expand on the prior art observations by demonstrating that atherosclerosis prone hypercholesterolemic mice ApoE–/– that also harbor a null mutation in either the adaptor molecule MyD88 or its upstream receptor TLR4 exhibit reduced aortic atherosclerosis, plaque lipid content, plaque macrophage infiltration, and cyclooxygenase (COX)-2 immunoreactivity without significantly altering circulating cholesterol levels or lipoprotein profiles. Evidence suggests that MyD88 deficiency leads to decreased levels of the circulating proinflammatory molecules IL-12p40 and/or MCP-1 and impaired leukocyte-EC adhesion in response to MM-LDL, which may contribute to the atheroprotective effects of MyD88 deficiency. These results implicate TLR4 and MyD88 mediated signaling as a pivotal link between hypercholesterolemia, inflammation, and atherosclerosis, and provide a foundation for the development of innovative therapeutic targets for prevention and therapy of atherosclerosis (Michelsen, K. S. et al. (2004) Proc. Natl. Acad. Sci. USA 101, 10679-10684). As such, available compounds that are known to inhibit TLR4 and/or MyD88 can be used in the treatment of human disease and injury.

Thus, the embodiments discussed herein are based on the surprising discovery that TLR4–/– animals and MyD88–/– animals develop substantially less atherosclerotic plaques in their coronary circulation than do wild-type TLR4 animals and wild-type MyD88 animals. The exemplary aspects discussed herein relate to therapeutic compositions and methods to inhibit TLR4 and MyD88 function for the treatment of various disease conditions. Various embodiments also relate to their use in pharmaceutical compositions intended for use in humans or veterinary medicine.

In various embodiments, a variety of TLR4 and/or MyD88 inhibitors are employed to inhibit the biological activity of TLR4 and/or MyD88. The TLR4 and/or MyD88 inhibitors according to the invention may be used to treat any disease condition. "Disease condition" includes any unhealthy condition of an animal (which includes human and non-human mammals), including various forms of inflammatory illnesses or diseases, such as atherosclerosis, transplant atherosclerosis, vein-graft atherosclerosis, stent restenosis, and angioplasty restenosis, and other cardiovascular diseases that atherosclerosis causes (hereinafter "vascular diseases"). "Vascular diseases" further includes any unhealthy condition of an animal (which includes human and non-human mammals), including angina pectoris and its subtypes (e.g., unstable angina and variant angina); ischemias affecting organs such as the brain, heart, bone, and intestines, and conditions associated with the ischemias, such as stroke, transient ischemic attacks, heart attack, osteonecrosis, colitis, poor kidney function, and congestive heart failure; poor blood circulation to the extremities and the complications of poor blood circulation, such as slow wound healing, infections, and claudication; atherosclerosis itself, including restenosis following angioplasty or stenting of atherosclerotic lesions; vein-graft atherosclerosis following bypass surgery; transplant atherosclerosis; and other diseases caused by or associated with atherosclerosis. Other applications will be recognized by one of skill in the art, and therefore are included herein. "Treating" or "treatment" of a disease condition in a mammal includes: (1) preventing the disease from occurring in a mammal which may be predisposed to the disease but does not yet experience or display symptoms of the disease; (2) Inhibiting the disease, i.e., arresting its development; (3) Relieving the disease, i.e., causing regression of the disease, or (4) providing any beneficial effect to a subject.

In various embodiments, the inhibitors may be administered to a mammal by any suitable means, such as those set forth in the various ensuing embodiments. Such inhibitors may include any compound, pharmaceutical, or other composition that effects an inhibition of the biological activity of TLR4 and/or MyD88.

In various embodiments, the TLR4 and/or MyD88 inhibitors according to the invention may be administered in a therapeutically effective amount. "Therapeutically effective amount" means that amount which, when administered to a mammal for treating a disease, is sufficient to effect such treatment for the disease. "Beneficial effect" as used herein refers to any effect on a patient, including, for example, ameliorating a disease, lessening the severity of its complications, preventing it from manifesting, preventing it from recurring, merely preventing it from worsening, or a therapeutic effort to affect any of the aforementioned, even if such therapeutic effort is ultimately unsuccessful.

In various embodiments, the compositions and methods discussed herein may be used in any patient who could benefit from reducing atherosclerosis that is already present, from inhibiting atherosclerosis that has yet to form, or from both reducing existing atherosclerosis and inhibiting new atherosclerosis. In the therapeutic indications discussed, supra, the compositions can advantageously be used in combination with other therapeutic interventions known to one of skill in the art. The use of the inhibitors described in various embodiments of the invention for treating vascular disease by combination therapy may also comprise the administration of the compound of the invention to a mammal in combination with common anti-inflammatory drugs, cytokines, or immunomodulators.

In various embodiments, methods for inhibiting TLR4 and/or MyD88 signaling using various peptide mimetics are provided. In one embodiment, the method involves the introduction of small peptides (i.e., peptides of approximately 10-20 amino acids) that bind to TLR4 receptors, thereby preventing these receptors from binding to MyD88. In another embodiment, the method involves the introduction of small peptides that bind endogenous MyD88. Short, overlapping segments (e.g., approximately 10-20 amino acids in length) of TLR4 and/or MyD88 may be separated to test which individual segments effect TLR4 and/or MyD88 cell signal transduction by binding to a MyD88 molecule, in the case of a TLR4 mimetic, or a TLR4 receptor, in the case of a MyD88 mimetic. Following separation, the segments are duplicated and tested to determine whether the segment comprises at least a portion of MyD88 that binds to a TLR4 receptor, or a portion of the TLR4 receptor that binds to MyD88. A segment suitable for use in accordance with the method discussed herein comprises at least a portion of MyD88 that binds to a TLR4 receptor, or at least a portion of the TLR4 receptor that binds MyD88, such that the administration of a sufficient amount of individual copies of this segment will hinder TLR4 and/or MyD88 signal transduction. Once administered, segments preferably bind to MyD88 binding sites of the TLR4 receptors, or bind to the endogenous MyD88, thereby preventing the TLR4 receptors from binding to the corresponding sites on MyD88, or preventing the endogenous MyD88 from binding to the corresponding site on the TLR4 receptor. This may significantly hinder TLR4 and/or MyD88 cell signal transduction.

In accordance with the method of the present invention, a segment that does, in fact, include at least a portion of MyD88 that binds to a TLR4 receptor may be administered to a patient for the treatment of a disease condition. In various embodiments, the portion of MyD88 may bind to the toll/IL-1 receptor binding domain of the TLR4 receptor. Similarly, in accordance with another method discussed herein, a segment that does, in fact, include at least a portion of the TLR4 receptor that binds to endogenous MyD88 may be administered to a patient for the treatment of a disease condition. In various embodiments, the portion of the TLR4 receptor may correspond to the toll/IL-1 receptor binding domain of the TLR4 receptor. Furthermore, it will be readily appreciated by one of such skill that a TLR4 and/or MyD88 peptide mimetic may be formulated in a variety of pharmaceutical compositions, any one of which may be suitable for use in accordance with the method of the present invention.

Administration may be performed by any suitable means, including via an oral form, such as a capsule, tablet, solution, or suspension; an intravenous form; an injectable form; an implantable form, such as a stent coating, a sustained release mechanism, or a biodegradable polymer unit; or any other suitable mechanism by which an active or therapeutic agent may be delivered to a patient. The dosage may similarly be determined in accordance with the selected form of administration, the level of which may be readily ascertained without undue experimentation, as can the most suitable means of administration.

The peptide mimetics as discussed in various embodiments refers to any structural analog of the TLR4 receptor and/or MyD88 molecule. Examples of suitable peptide mimetics include but are not limited to CRX-675 (available from Corixa; Seattle, Wash.), RP105 (Divanovic, S. et al. (2005) *Nature Immunology*), ST2 effector molecule (Brint, E. K. et al. (2004) *Nature Immunology* 5, 373-379), various vaccinia virus ORFs such as A46R and A52R (Bowie, A. et al. (2000) *Proc. Acad. Natl. Sci. USA* 97, 10162-10167), hydrocinnamoyl-L-valyl pyrrolidine (Bartfai, T. et al. (2003) *Proc. Natl. Acad. Sci. USA* 100, 7971-7976). Other peptide mimetics will be readily recognized by one of skill in the art.

In various embodiments, a method of inhibiting MyD88 expression through the introduction of an anti-MyD88 antibody is provided. In other embodiments, a method of inhibiting TLR4 expression through the introduction of an anti-TLR4 antibody is provided. Any suitable anti-TLR4 and/or anti-MyD88 antibody may be used in conjunction with this aspect of the present invention, including, but in no way limited to, anti-TLR4 and/or anti-MyD88 antibodies, and any suitable derivatives thereof, equivalents thereof, or compounds with active sites that function in a manner similar to anti-TLR4 and/or anti-MyD88 antibodies, whether those compounds are naturally occurring or synthetic (all hereinafter included within the phrase "anti-TLR4 and/or anti-MyD88 antibodies"). In various embodiments, the anti-TLR4 and/or anti-MyD88 antibodies may target the toll/IL-1 receptor binding domain of the TLR4 receptor or the portion of MyD88 that binds to the toll/IL-1 receptor binding domain of the TLR4 receptor.

An appropriate quantity of an anti-TLR4 and/or anti-MyD88 antibody necessary to effect the method of the present invention, and the most convenient route of delivering the same to a mammal may be determined by one of ordinary skill in the art, without undue experimentation. Furthermore, it will be readily appreciated by one of such skill that an anti-TLR4 and/or anti-MyD88 antibody may be formulated in a variety of pharmaceutical compositions, any one of which may be suitable for use in accordance with the method of the present invention.

Such an antibody may be delivered to a mammal through any conventional mechanism in a therapeutically effective amount to inhibit TLR4 and/or MyD88 signaling in a mammal; the mechanism of delivery and quantity of antibody necessary for inhibiting TLR4 and/or MyD88 expression both being readily ascertainable without undue experimentation.

Examples of suitable anti-TLR4 and/or anti-MyD88 antibodies include but are not limited to anti-TLR4 antibody product numbers ab8376, ab2891, ab6563, ab6726, ab6728, ab6729, ab6785, ab6788, ab7002, ab7018 and HTA125 (available from Abcam; Cambridge, UK); MTS510 (available from Monosan; Netherlands); anti-MyD88 antibody product numbers ab2064 and ab2068 (available from Abcam); anti-MyD88 antibody catalog number 2125 (available from ProSci Incorporated; Poway, Calif.); anti-MyD88 antibody product number M9934 (available from Sigma; St. Louis, Mo.). Other anti-TLR4 and/or anti-MyD88 antibodies will be readily recognized by one of skill in the art.

In various embodiments, the antibodies of the invention may be screened to determine their effectiveness in binding the target area of TLR4 and/or MyD88. Techniques are known in the art for screening antisera that are suitable (Sambrook, J. & D. W. Russel, Molecular Cloning: A Laboratory Manual, Vol. 2, $3^{rd}$ ed., A14.50-14.51 (2001)). For example, commone techniques may include performing western blot analysis for reactivity of antisera with a protein of interest, immunoprecipitation assays or radioimmunoassays.

With the advent of small-molecule antagonists, it may be feasible to evaluate the efficacy of therapeutic inhibition of TLR signaling in treating atherosclerosis-based pathologies. Small-molecule antagonists are known in the art (Bartfai, T., et al. (2003) *Proc. Natl. Acad. Sci. USA* 100, 7971-7976). Specifically, molecules of the toll-interleukin 1 receptor (TIR) superfamily that do not activate NF-κB have been shown to negatively regulate TLR4 signaling (Brint, E. K. et al., (2004) *Nature Immunology* 5, 373-379). Furthermore, various compositions are known in the art to block NF-κB and negatively regulate TLR signaling (O'Neill, L. (2003) *Current Opinion in Pharmacology* 3, 396-403; O'Neill, L. (2004) *Trends in Immunology* 25, 687-693; Liew, F. Y. et al. (2005) *Immunol Lett.* 96, 27-31). Other compositions and inhibitors will be recognized by one of skill in the art, and therefore are included herein. Still further, analogous examples of receptor ligands and antibodies used to antagonize signaling transduction pathways are known in the art. For example, neutralizing antibodies to specific chemokines and receptor-ligand antagonists that compete with specific chemokines for binding domains without activating the receptors towards eliciting a functional response are discussed in the art (Howard et al. (1996) Trend Biotechnol 14, 46-51). Specifically, the use of anti-chemokine antibodies has been shown to curtail inflammation in a number of animal models (e.g., anti-MIP-1α in bleomycin-induced pulmonary fibrosis (Smith et al., (1994) Leukocyte Biol 57, 782-787); anti-IL-8 in reperfusion injury (Sekido et al. (1995) Nature 365, 654-657), and anti-MCP-1 in a rat model of glomerulonephritis (Wada et al. (1996) FASEB J 10, 1418-1425)). Further, several small molecule antagonists of chemokine receptor function have been reported in the scientific and patent literature (White, J. (1998) Biol Chem 273, 10095-10098; Hesselgesser, J. (1998) Biol Chem 273, 15687-15692; Bright et al. (1998) BioorgMed Chem Lett 8, 771-774; Lapierre, 26th Natl Med Chem Symposium, June 14-18, Richmond (Va.), USA (1998); Forbes et al. (2000) Bioorg Med Chem Lett 10, 1803-18064; Kato et al., WO 97/24325; Shiota et al., WO 97/44329; Naya et al., WO 98/04554; Schwender et al., WO 98/02151; Hagmann et al., WO 98/27815; Connor et al., WO 98/06703; Wellington et al., U.S. Pat. No. 6,288,103).

One such alternative embodiment contemplated by the present invention includes methods for inhibiting TLR4 and/or MyD88 signaling using various statins (Methe, H. et al. (2005) *Arterioscler Thromb Vasc Biol.* 25, 1-7). Atorvastatin (available from Pfizer; Ann Arbor, Mich.) and Simvastatin (available from Merck; West Point, Pa.) are examples. Any suitable statin may be used in conjunction with this aspect of the present invention, including, but in no way limited to, statins now known or discovered in the future to act upon the TLR4 and/or MyD88 signaling pathways, and any suitable derivatives thereof, equivalents thereof, or compounds with active sites that function in a manner similar to statins, whether those compounds are naturally occurring or synthetic (all hereinafter included within the phrase "statins"). Still other inhibitors of the TLR4 and/or MyD88 signaling pathways are included in the present invention, for example, but not limited to, the ST2 effector molecule (Brint, E. K. et al. (2004) *Nature Immunology* 5, 373-379), anti-apoptotic protein A20 (Arvelo, M. B. et al. (2002) *Hepatology* 35, 535-543), soluble TLR4, agonistic lipid A and its analogues (O'Neill, L. (2003) *Current Opinion in Pharmacology* 3, 396403), inhibitors of 1-KB-2 (Epinat, J. C. et al. (1999) *Oncogene* 18, 6896-6909; Haefner, B. (2002) *Drug Discov Today* 7, 653-663), salicylate and parthenolide (Koop, E. et al. (1994) *Science* 265, 956-959; Almawi, W. Y. et al. (2002) *J Mol Endocrinol* 28, 69-78), PS-1145 (Epinat, J. C. et al. (1999) *Oncogene* 18, 6896-6909), inhibitors of p38 and JNK (Boehm, J. C. et al. (2000) *Expert Opin Ther Pat* 10, 25-37; English, J. M. et al. (2002) *Trends Pharmacol Sci* 23, 40-45), inhibitors of IL-1 receptor-associated kinase 4 and inhibitors of TGF-beta activated kinase 1. Other compositions and inhibitors will be recognized by one of skill in the art, and therefore are included herein.

An appropriate quantity of statin and the above-mentioned inhibitors necessary to effect the method of the present invention, and the most convenient route of delivering the same to a mammal may be determined by one of ordinary skill in the art, without undue experimentation (Methe, H. et al. (2005) *Arterioscler Thromb Vasc Biol.* 25, 1-7; O'Neill, L. (2003) *Current Opinion in Pharmacology* 3, 396-403; Brint, E. K. et al. (2004) *Nature Immunology* 5, 373-379). Furthermore, it will be readily appreciated by one of such skill that statins may be formulated in a variety of pharmaceutical compositions, any one of which may be suitable for use in accordance with the method of the present invention.

Such statins and above-mentioned inhibitors may be delivered to a mammal through any conventional mechanism in a therapeutically effective amount to inhibit TLR4 and/or MyD88 signaling in a mammal; the mechanism of delivery and quantity of statin necessary for inhibiting TLR4 and/or MyD88 expression both being readily ascertainable without undue experimentation (Methe, H. et al. (2005) *Arterioscler Thromb Vasc Biol.* 25, 1-7; O'Neill, L. (2003) *Current Opinion in Pharmacology* 3, 396-403; Brint, E. K. et al. (2004) *Nature Immunology* 5, 373-379).

In various embodiments, the present invention provides pharmaceutical compositions comprising a pharmaceutically acceptable excipient and a therapeutically effective amount of at least one inhibitor used in connection with the exemplary aspects discussed herein. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs that it may come in contact with, meaning that it must not carry a risk of toxicity, irritation, allergic response, immunogenecity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20$^{th}$ edition, Williams & Wilkins PA, USA) (2000).

EXAMPLES

Example 1

Generation of ApoE/MyD88 and ApoE/TLR4 Double Knockout Mice

ApoE-deficient C57BL/6 mice were obtained from The Jackson Laboratory. MyD88−/− and TLR4−/− mice were kindly provided by S. Akira (Osaka University, Osaka). Both strains were backcrossed for four generations into the C57BL/6 strain. MyD88−/− and TLR4−/− mice were crossed with ApoE−/− C57BL/6 mice. Heterozygous mice were intercrossed to generate homozygous ApoE−/− mice bearing combinations of MyD88+/+, +/−, −/−, and TLR4+/+ and −/− mice. This process results in a total backcross of five generations onto the C57BL/6 background. Male and female mice were fed a high (0.15%)-cholesterol diet (Harlan Teklad, Madison, Wis.) for 6 months.

Example 2

Assessment of Atherosclerosis in Aortas and Aortic Sinus

Aortas were excised, adherent (adventitial) fat was removed, and were then fixed in HistoCHOICE (obtained from Amrecso; Solon, Ohio). Whole aortas were opened longitudinally from the aortic arch to the iliac bifurcation, mounted en face, and stained for lipids with Oil red O. Hearts were embedded in OCT compound (Tissue Tek, obtained from Sakura; Torrance, Calif.) and cross sections of the aortic sinus were stained with Oil red O. Lesion areas were quantified with IMAGEPRO PLUS (obtained from Media Cybernetics; Silver Spring, Md.). Image analysis was performed by a trained observer blinded to the genotype of the mice. To assess macrophage infiltration into atherosclerotic plaques, frozen sections of aortic sinuses were fixed, incubated with 3% hydrogen peroxide, and permeabilized. The sections were incubated with MOMA-2, a macrophage-specific antibody, or control IgG antibody (obtained from Serotec; Raleigh, N.C.). For visualization, 3-amino-9-ethyl-carbazole chromogen (obtained from DAKO; Carpinteria, Calif.) was used as a substrate (Fredrikson, G. N., et al. (2003) *Arterioscler. Thromb. Vasc. Biol.* 23, 879-884). MOMA-2 macrophage immunopositive areas were quantified with IMAGEPRO PLUS.

Example 3

COX-2 Staining

Sections were blocked in 0.1 M Tris.HCl/0.15 M NaCl/0.5% blocking reagent (TNB blocking buffer) and incubated with primary COX-2 or control IgG antibody (obtained from Santa Cruz Biotechnology; Santa Cruz, Calif.) diluted in TNB blocking buffer at 4° C. overnight (1:5,000 dilution), followed by incubation with streptavidin-horseradish peroxidase complex. The signal was enhanced by using the tyramide signal amplification kit (obtained from NEN Life Science Products; Boston, Mass.) according to the manufacturer's recommendations and sections were counterstained for nuclei with 100 nM SYTOX green (obtained from Molecular Probes; Eugene, Oreg.).

Example 4

Lipid Profiles

Sera from mice were obtained at the time of killing, after an overnight fast. Total cholesterol concentrations were determined in duplicate by using a calorimetric assay (infinity cholesterol reagent, obtained from Sigma Diagnostics; St. Louis, Mo.). Triglyceride concentrations were determined by using the L-type triglyceride H assay according to the manufacture's instructions (obtained from Wako Chemicals USA; Richmond, Va.). Lipoprotein profile was determined by using high performance liquid chromatography (HPLC).

Example 5

Functional Studies in Isolated Murine Aortic Ecs

Thoracic aortas from MyD88−/− and MyD88+/+ mice were cleaned and cut into 3-mm-long rings. These segments were turned inside-out and placed in tissue culture dishes coated with collagen type I (obtained from BD Biosciences; Bedford, Mass.) and incubated in MCDB131 (obtained from Invitrogen; Carlsbad, Calif.) supplemented with 20% FBS (obtained from Omega Scientific; Tarzana, Calif.), 1% antibiotic/antimycotic solution (obtained from Invitrogen), 1 unit/ml heparin (obtained from Sigma), and 60 μg/ml EC growth supplement (obtained from Upstate; Charlottesville, Va.). The vessel rings were removed once cell outgrowth was observed. The identity of cells was confirmed by staining with von Willebrand factor (obtained from DAKO) and by 1,1'-dioctadecyl-3,3,3',3'-tetramethylindocarbocyanine-acetylated LDL (obtained from Molecular Probes) uptake experiments (purity of ECs>95%). For adhesion assays ECs were grown to confluency. The cells were stimulated with MM-LDL, native LDL, LPS, or tumor necrosis factor (TNF)-α in culture medium containing 1% lipoprotein-deficient serum for 6 h. After incubation, cells were washed with medium without serum and incubated with human peripheral blood mononuclear cells labeled with 5 μM 2',7'-bis-(2-carboxyethyl)-5-(and -6)-carboxyfluorescein, acetoxymethyl ester (obtained from Molecular Probes) for 1 h. Cells were washed and lysed with 0.5 N NaOH. Fluorescence was measured in a fluorescence microplate reader (excitation, 485 nm; emmission, 528 nm).

Example 6

Serum Levels of Cytokines and Chemokines

IL-10, IL-12p40, MCP-1, and chemokine KC concentrations in the sera of mice were measured by ELISAs according to the manufacturer's instructions (obtained from BD Biosciences for IL-10, IL-12p40, and MCP-1 and R & D Systems for KC).

Example 7

Statistical Analysis

Data are expressed as mean ±SD. Statistical significance was determined by one-factor ANOVA with Bonferroni correction and Student's t test. P<0.05 was considered to be statistically significant.

Example 8

MyD88 Deficiency Does Not Alter Circulating Cholesterol or Lipoprotein Profiles in ApoE−/− Mice To study the role of MyD88 on the development of atherosclerosis, double knockout mice were generated by intercrossing ApoE−/− and MyD88−/− mice, backcrossed onto the C57BL/6 strain for at least five generations to enhance congenicity and reduce secondary sources of variance. ApoE−/−/MyD88−/− and littermate controls (ApoE−/−/MyD88+/− and ApoE−/−/MyD88+/+) were fed a high-cholesterol diet and were killed at 6 months. To evaluate the effect of MyD88 on plasma lipid concentrations, total serum cholesterol concentrations were measured. No significant differences in total cholesterol or plasma triglyceride concentrations were found between the genotypes at 24 weeks of age (data not shown). There was no significant effect of MyD88 deficiency on lipoprotein profiles (data not shown).

Example 9

Figure 1A:
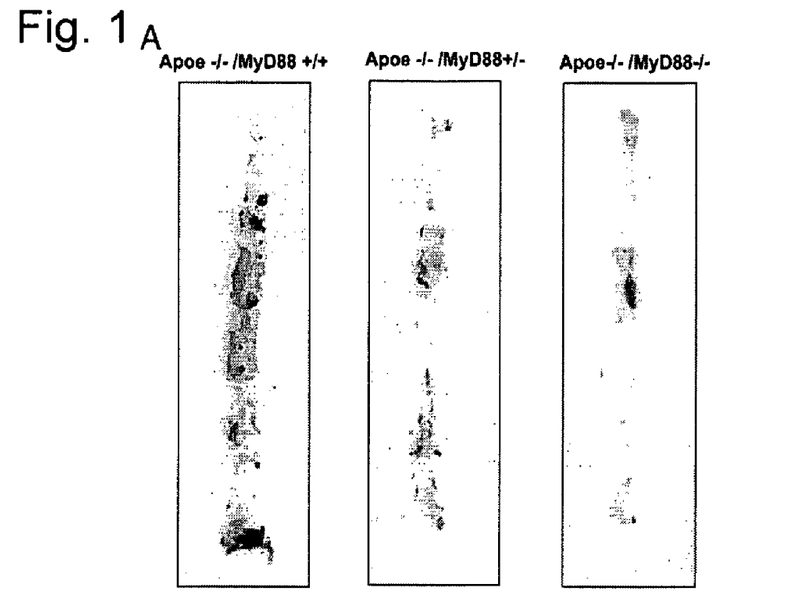
FIG. 1A depicts a series of photomicrographs of aortas of ApoE−/−/MyD88−/−, ApoE−/−/MyD88+/−, and ApoE−/−/MyD88+/+ mice fed with a high-cholesterol diet for 6 months. Aortas were isolated and stained for lipid deposition with Oil red O. Representative specimens from the three groups are shown.
Figure 1B:
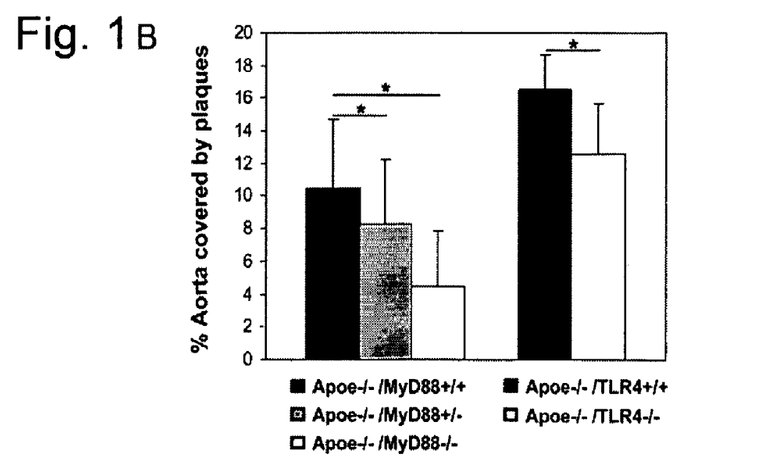
FIG. 1B shows the quantification of plaque areas in whole aortas in ApoE−/−/MyD88−/− (Left) and ApoE−/−/TLR4−/− (Right) mice. Aortas of ApoE−/−/MyD88−/−, ApoE−/−/MyD88+/−, ApoE−/−/MyD88+/+, ApoE−/−/TLR4−/−, and ApoE−/−/TLR4+/+ mice were stained for lipid deposition with Oil red O. Means and SD (n=13 for ApoE−/−/MyD88−/−, ApoE−/−/MyD88+/−, ApoE−/−/MyD88+/+; n=8 for ApoE−/−/TLR4+/+; and n=12 for ApoE−/−/TLR4−/−) of plaque areas are shown. Total plaque area in MyD88−/− or TLR4−/− was significantly reduced compared with corresponding wild-type mice (*, P<0.01).

MyD88 Deficiency Reduces the Extent of Aortic Atherosclerosis in ApoE−/− Mice ApoE−/− mice fed an atherogenic diet develop atherosclerotic lesions with morphological characteristics similar to those seen in humans (Breslow, J. L. (1996) *Science* 272, 685-688). To evaluate the effect of MyD88 deficiency on the extent of aortic atherosclerosis, the total lesion area was measured by using en face preparation of the aorta and Oil red O staining for lipids (FIG. 1A). Computer-assisted quantitative histomorphometric analysis revealed a 57% reduction in the extent of atherosclerosis in ApoE−/−/MyD88−/− mice. The extent of atherosclerosis in the ApoE−/−/MyD88+/− mice was intermediate between that observed in ApoE−/−/MyD88=+/+ and ApoE−/−/MyD88−/− mice, which is consistent with a gene dose-response effect (FIG. 1B, Left). The atheroprotective effect of MyD88 deficiency was observed in male as well as in female mice.

Example 10

Figures 2A, 2B, 2C, 2D:
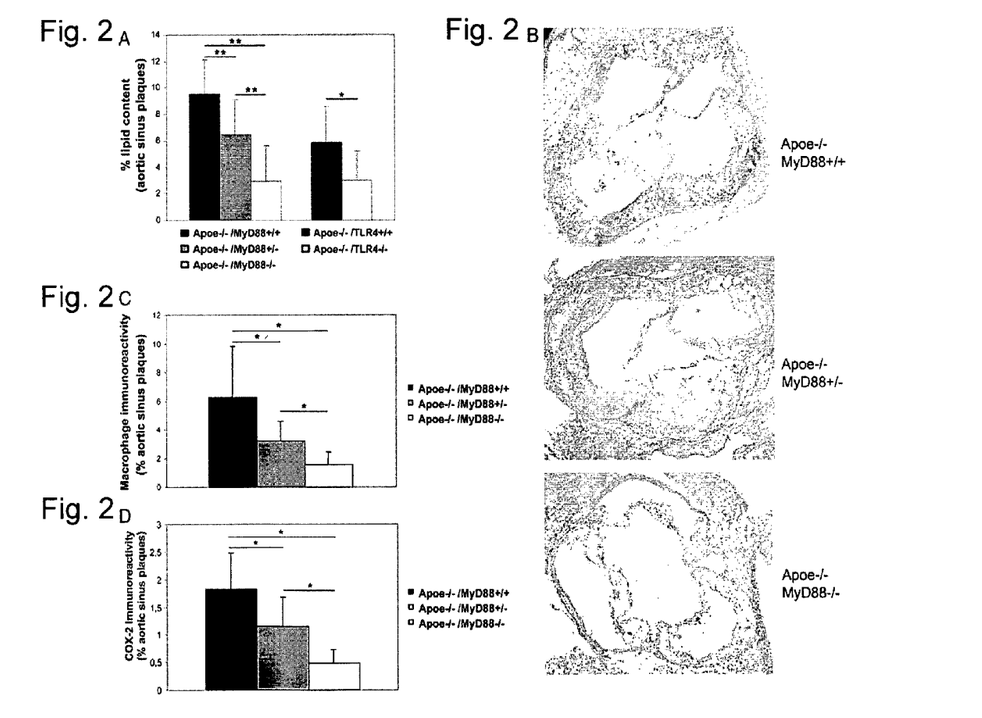
FIG. 2A shows the quantification of the lipid content in aortic plaques from ApoE−/−/MyD88−/−, ApoE−/−/MyD88+/−, and ApoE−/−/MyD88+/+ (Left) and ApoE−/−/TLR4−/− and ApoE−/−/TLR4+/+ (Right) mice. Shown are means and SD of the percentage of lipid content relative to total plaque areas (n=10 for ApoE−/−/MyD88−/−, ApoE−/−/MyD88+/− and ApoE−/−/MyD88+/+; n=7 for ApoE−/−/TLR4+/+; and n=8 for ApoE−/−/TLR4−/−). Relative lipid content in ApoE−/−/MyD88−/− or ApoE−/−/TLR4−/− is significantly reduced compared with corresponding wild-type mice (**, p<0.01; *, P<0.05).
FIG. 2B depicts a series of photomicrographs of representative MOMA-2 staining of aortic sinus plaques from ApoE−/−/MyD88−/−, ApoE−/−/MyD88+/−, and ApoE−/−/MyD88+/+ mice.
FIG. 2C shows the quantitative analysis of macrophage immunoreactivity in aortic sinus plaques of ApoE−/−/MyD88−/−, ApoE−/−/MyD88+/−, and ApoE−/−/MyD88+/+ mice, expressed as a proportion of the total plaque areas (n=10 in each group). Means and SD are shown (*, P<0.01).
FIG. 2D shows the quantitative analysis of COX-2 immunofluorescent staining in sclerotic plaques of ApoE−/−/MyD88−/−, ApoE−/−/MyD88+/−, and ApoE−/−/MyD88+/+ mice (n=7 in each group). Means and SD are shown (*, P<0.01).

MyD88 Deficiency is Associated with Reduction in Plaque Lipid Content, Macrophage Infiltration, and COX-2 Immunoreactivity To examine the effect of MyD88 deficiency on the composition of atherosclerotic plaques, lipid content was examined with Oil red 0 histochemical staining and the extent of macrophage infiltration was examined with MOMA-2 immunostaining in aortic sinus plaques of ApoE−/−/MyD88−/−, ApoE−/−/MyD88+/−, and ApoE−/−/MyD88+/+ mice. Aortic sinus plaques of ApoE−/−/MyD88−/− mice exhibited significantly less lipid and macrophage accumulation than plaques of ApoE−/−/MyD88+/+ mice (69% and 75% reduction, respectively). Intermediate levels were observed in ApoE−/−/MyD88+/− mice (FIG. 2A Left, and B and C), which was again consistent with a gene dose-response relationship. Quantification of lesion size of aortic sinus plaques revealed a significant reduction of lesion size in ApoE−/−/MyD88−/− compared with ApoE−/−/MyD88+/+ mice (P<0.05, data not shown). COX-2 immunostaining was assessed in the aortic sinus plaques of ApoE−/−/MyD88−/−, ApoE−/−/MyD88+/−, and ApoE−/−/MyD88+/+ mice to determine whether reduction in the extent of atherosclerosis produced by MyD88 deficiency is accompanied by decreased expression of the proinflammatory enzyme COX-2. Lesions from ApoE−/−/MyD88+/+ mice showed extensive COX-2 immunostaining, which was markedly less in ApoE−/−/MyD88−/− mice (FIG. 2D). Intermediate levels of COX-2 immunoreactivity were observed in ApoE−/−/MyD88+/− mice (FIG. 2D).

Example 11

MyD88 Deficiency is Associated with Reduced Circulating Levels of the Inflammatory Cytokine IL-12 and MCP-1

Figure 3A:
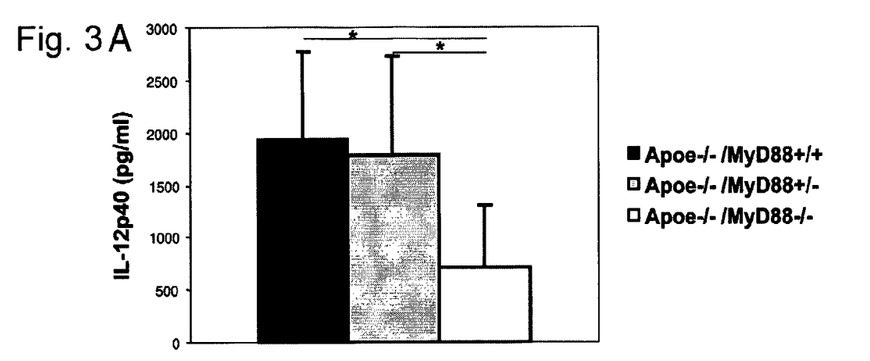
FIG. 3A shows IL-12p40 serum concentrations of ApoE−/−/MyD88−/−, ApoE−/−/MyD88+/−, and ApoE−/−/MyD88+/+ mice fed with a high-cholesterol diet for 6 months (n=19 in each group).
Figure 3B:
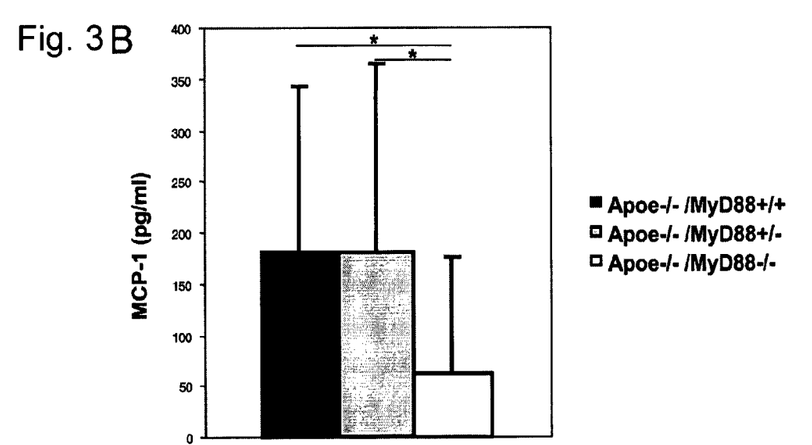
FIG. 3B shows MCP-1 serum concentrations of ApoE−/−/MyD88−/−, ApoE−/−/MyD88+/−, and ApoE−/−/MyD88+/+ mice (n=24 in each group). Means and SD are shown (*, P<0.01).

The effect of MyD88 deficiency in inhibiting atherogenesis by a general antiinflammatory mechanism was tested. MyD88 deficiency altered circulating concentrations of key proinflammatory cytokines and chemokines (T helper 1 cytokine IL-12 and MCP-1) in ApoE−/− mice. ApoE−/−/MyD88−/− mice had markedly reduced serum levels of IL-12p40 and MCP-1 compared with ApoE−/−/MyD88+/+ mice (FIG. 3A and FIG. 3B). IL-12p40 serum concentrations of ApoE−/−/MyD88+/− mice were comparable with the serum concentrations of wild-type ApoE−/−/MyD88+/+. Serum concentrations of MCP-1 in ApoE−/−/MyD88+/− mice were comparable with those of wild-type ApoE−/−/MyD88+/+ mice. MyD88 deficiency was not associated with any significant changes in the circulating concentrations of the antiinflammatory cytokine IL-10 or the chemokine KC (data not shown). These results appear most consistent with the interpretation that at least part of the suppression of atherogenesis observed in mice with both ApoE and MyD88 deficiency may be mediated by a general reduction in circulating levels of proatherogenic inflammatory molecules.

Example 12

Figure 4:
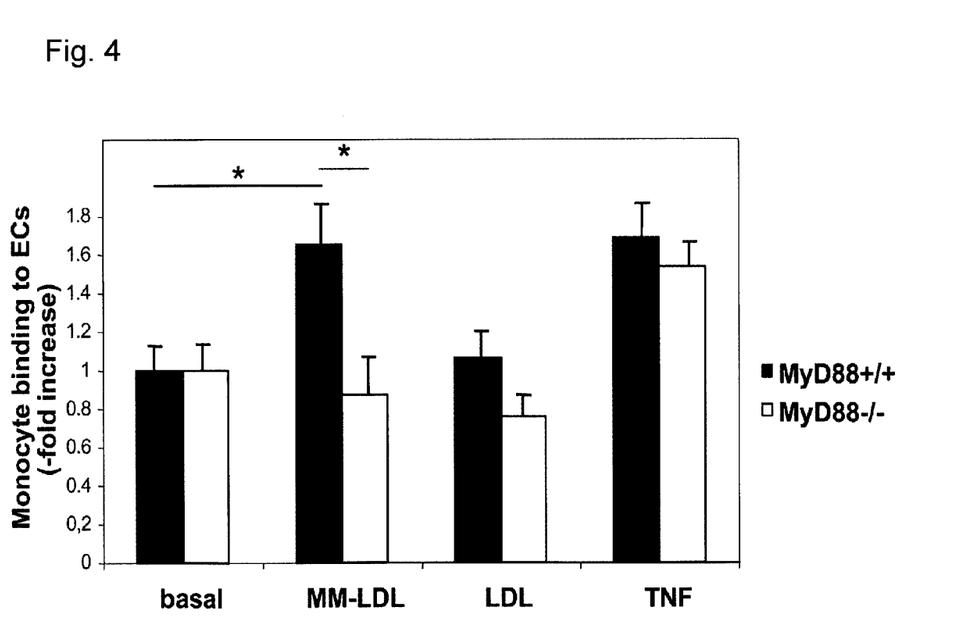
FIG. 4 shows that endothelial cells (Ecs) from MyD88-deficient mice exhibit reduced MM-LDL-induced adhesion of leukocytes in accordance with an embodiment of the invention. Adhesion of human peripheral blood mononuclear cells to murine aortic ECs derived from aortas of MyD88−/− or MyD88+/+ mice stimulated with MM-LDL, LDL, or TNF-α. Data from one of three representative experiments with similar results are shown as fold increase in leukocyte adhesion over background (*, P<0.05).

MyD88 Deficiency is Associated with Reduced Adhesion of Leukocytes to ECs upon Stimulation with MM-LDL Enhanced leukocyte-EC adhesion constitutes one of the pivotal early events in development of atherosclerotic plaques. To determine the effect of MyD88 deficiency on leukocyte-EC adhesion, aortic ECs were isolated from MyD88−/− and MyD88+/+ mice and their interaction with leukocytes (human peripheral blood mononuclear cells) was assessed upon stimulation with MM-LDL. ECs from the aortas of MyD88+/+ mice showed a dose-dependent increase in leukocyte adhesion when stimulated with MM-LDL, but not with unmodified native LDL (FIG. 4). In contrast, leukocyte adhesion to ECs derived from MyD88-deficient mice did not increase in response to stimulation with either MM-LDL or LDL. However, TNF-α-induced leukocyte adhesion to ECs was not impaired in MyD88−/− ECs and was not different from leukocyte adhesion to MyD88+/+ECs. These results suggest that impaired leukocyte adhesion to MM-LDL-stimulated MyD88−/− ECs may lead to reduced infiltration of mononuclear phagocytes into developing plaques of ApoE−/−/MyD88−/− mice.

Example 13

TLR4 Deficiency Reduces the Extent of Aortic Atherosclerosis in ApoE−/− Mice

To elucidate further the role of MyD88 and upstream receptor(s) on the development of atherosclerosis, double knockout mice were generated by intercrossing ApoE−/− and TLR4−/− mice. ApoE−/−/TLR4−/− and littermate controls (ApoE−/−/TLR4+/+) were fed a high-cholesterol diet and were killed at 6 months. Total serum cholesterol and triglyceride concentrations were measured and, as was the case with mice deficient in both ApoE and MyD88, no significant differences were found in total cholesterol or plasma triglyceride concentrations between genotypes (data not shown). The total lesion area of whole aortas was measured after Oil red O staining. Quantitative analysis revealed a 24% reduction in the extent of atherosclerosis in ApoE−/−/TLR4−/− mice (n=12 for ApoE−/−/TLR4−/− and n=8 for ApoE−/−/TLR4+/+, P<0.01; FIG. 1B Right).

Example 14

Figure 5A:
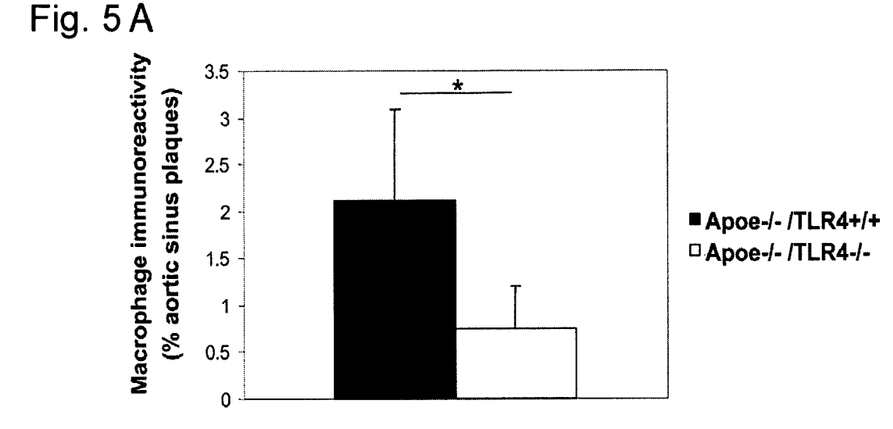
FIG. 5A shows the quantitative analysis of macrophage immunoreactivity in aortic sinus plaques of ApoE−/−/TLR4−/− and ApoE−/−/TLR4+/+ mice, expressed as a proportion of the total plaque areas (n=7 per group). Means and SD are shown (*, P<0.01).
Figure 5B:
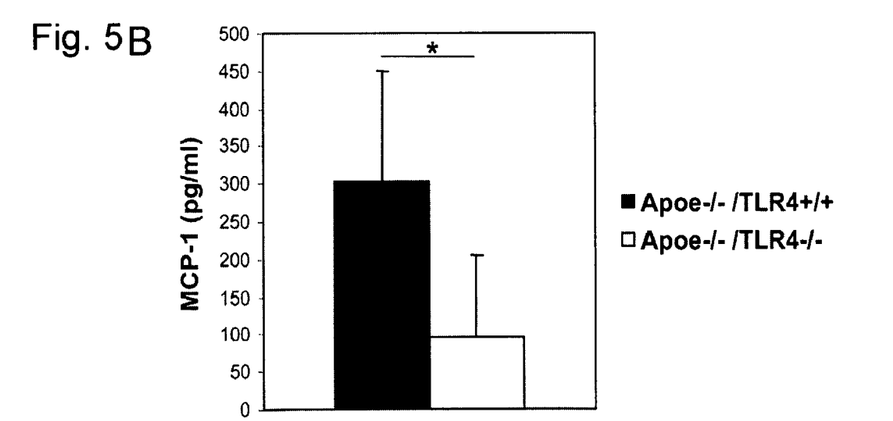
FIG. 5B shows MCP-1 serum concentrations of ApoE−/−/TLR4−/− and ApoE−/−/TLR4+/+ mice (n=8 for ApoE−/−/TLR4+/+ and n=14 for ApoE−/−/TLR4−/−). Means and SD are shown (*, P<0.01).

TLR4 Deficiency is Associated with Reduction in Plaque Lipid Content, Macrophage Infiltration, and MCP-1 Serum Concentration To further explore the characteristics of atherosclerosis in ApoE−/−/TLR4−/− mice, lipid content and macrophage infiltration were quantified in aortic sinus plaques (FIGS. 2A Right panel and 5A). The lipid content of aortic sinus plaques was significantly reduced in ApoE−/−/TLR4−/− mice (55% reduction). Macrophage infiltration in ApoE−/−/TLR4−/− mice was also significantly reduced by 65% compared with control mice. Furthermore, MCP-1 serum concentrations were significantly reduced in ApoE−/−/TLR4−/− mice (FIG. 5B). In contrast to ApoE−/−/MyD88−/− mice, there was no significant differences in IL-12p40 serum concentrations between ApoE−/−/TLR4−/− and ApoE−/−/TLR4+/+ mice (data not shown).

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

What is claimed is:

1. A method of treating a vascular disease in a subject, comprising:
   (a) providing a composition comprising at least one toll-like receptor 4 (TLR4) inhibitor selected from the group consisting of hydrocinnamoyl-L-valyl pyrrolidine, anti-TLR4 antibodies ab8376 and MTS510, and combinations thereof, and at least one myeloid differentiation factor 88 (MyD88) inhibitor selected from hydrocinnamoyl-L-valyl pyrrolidine; and
   (b) administering said composition to said subject in an amount effective to treat the vascular disease.

2. The method of claim 1, wherein the vascular disease is selected from the group consisting of atherosclerosis, transplant atherosclerosis, vein-graft atherosclerosis, thrombosis, restenosis, stent restenosis, and angioplasty restenosis.

3. The method of claim 1, wherein said subject is a human.

4. The method of claim 1, wherein the route of administration is oral, parenteral or via implantation.

5. The method of claim 1, wherein administering the composition further comprises delivering the composition with an intravascular device.

6. The method of claim 5, wherein the intravascular device is a catheter or a stent.

7. The method of claim 6, wherein the intravascular device is coated with the composition.

8. The method of claim 1, where the disease is atherosclerosis.

9. The method of claim 1, wherein said composition includes a pharmaceutically acceptable carrier.

10. The method of claim 1, wherein the TLR4 inhibitor is hydrocinnamoyl-L-valyl pyrrolidine.

11. The method of claim 1, wherein the TLR4 inhibitor is anti-TLR4 antibody ab8376.

12. The method of claim 1, wherein the TLR4 inhibitor is anti-TLR4 antibody MTS510.

13. The method of claim 1, wherein the MyD88 inhibitor is hydrocinnamoyl-L-valyl pyrrolidine.

* * * * *